United States Patent [19]

Sangokoya

[11] Patent Number: 5,235,081

[45] Date of Patent: Aug. 10, 1993

[54] METHOD OF REMOVING GEL FORMING MATERIALS FROM METHYLALUMINOXANES

[75] Inventor: Samuel A. Sangokoya, Baton Rouge, La.

[73] Assignee: Ethyl Corporation, Richmond, Va.

[21] Appl. No.: 853,239

[22] Filed: Mar. 18, 1992

[51] Int. Cl.$^5$ ............................................. C07F 5/06
[52] U.S. Cl. .................... 556/179; 556/182; 556/190; 502/117; 502/152
[58] Field of Search ............... 556/179, 182, 190

[56] References Cited

U.S. PATENT DOCUMENTS

| | | |
|---|---|---|
| 3,135,705 | 6/1964 | Vandenberg ............................ 260/2 |
| 3,152,105 | 10/1964 | Long ................................... 260/88.2 |
| 3,300,458 | 1/1967 | Manyik et al. ....................... 260/88.2 |
| 4,658,078 | 4/1987 | Slaugh et al. ........................ 585/512 |
| 4,730,071 | 3/1988 | Schoenthal et al. ................. 556/179 |
| 4,730,072 | 3/1988 | Schoenthal et al. ................. 556/179 |
| 4,772,736 | 9/1988 | Edwards et al. ..................... 556/179 |
| 4,908,463 | 3/1990 | Bottelberghe ....................... 556/179 |
| 5,015,749 | 5/1991 | Schmidt et al. ..................... 556/179 |
| 5,084,585 | 1/1992 | Maezawa et al. ................... 556/179 |
| 5,093,295 | 3/1992 | Tomotsu et al. .................... 502/152 |
| 5,157,137 | 10/1992 | Sangokoya ........................... 556/179 |

FOREIGN PATENT DOCUMENTS 279586 8/1988 European Pat. Off. .

Primary Examiner—José G. Dees
Assistant Examiner—Porfirio Nazario
Attorney, Agent, or Firm—David M. Bunnell

[57] ABSTRACT

Gel and gel forming materials are removed from methylaluminoxane by mixing an aromatic hydrocarbon solvent solution of the methylaluminoxane with an aliphatic hydrocarbon solvent and then separating the precipitated solids from the methylaluminoxane solution.

21 Claims, No Drawings

METHOD OF REMOVING GEL FORMING MATERIALS FROM METHYLALUMINOXANES

This invention relates generally to alkylaluminoxanes and more specifically to a method for providing aromatic solvent soluble methylaluminoxane by fractionation of the methyl-aluminoxane to remove gel and gel forming materials.

Manyik, et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Schoenthal, et al. U.S. Pat. No. 4,730,071 describe the preparation of methylaluminoxane by dispersing water in toluene using an ultrasonic bath to cause the dispersion and then adding a toluene solution of trimethylaluminum to the dispersion. Schoenthal, et al. U.S. Pat. No. 4,730,072 is similar except it uses a high speed, high shear-inducing impeller to form the water dispersion.

Edwards, et al. U.S. Pat. No. 4,722,736 describe an aluminoxane process in which water is introduced below the surface of a solution of hydrocarbyl aluminum adjacent to a stirrer which serves to immediately disperse the water in the hydrocarbon 2solution.

Bottelberghe, U.S. Pat. No. 4,908,463 describes the preparation of methylaluminoxane in which a trimethylaluminum/toluene solution and a xylene/water dispersion are fed to a T-shaped reactor.

A problem associated with free water addition to trimethylaluminum to produce methylaluminoxane solutions in organic solvents is that the solutions usually contain gel and small particles or other marginally soluble components which aggregate to form gel on standing. Even when the solvent is an aromatic hydrocarbon such as toluene and the particles and/or gel are removed by filtration, additional gel can form in the solution after 2 or 3 weeks, especially when originally prepared dilute solutions are concentrated to higher aluminoxane contents which are more economic for storage, shipment and use. A process has now been found that not only will remove gel from methylaluminoxane solutions but also removes materials which separate and form solids or gel in the solution on standing.

European Patent Application 279,586 discloses the preparation of finely divided aluminoxane by adding aliphatic solvents to aromatic solvent solutions of aluminoxanes in order to precipitate the aluminoxane as finely divided particles. Preferably, an aliphatic solvent having a higher boiling point than the aromatic solvent is used so that the aromatic solvent can be removed to facilitate precipitation. This process does not separate insoluble material from the aluminoxane or otherwise fractionate the aluminoxane as is provided for by the invention.

In accordance with this invention there is provided a process for removing gel and gel forming materials from methylaluminoxane; said process comprising mixing an aromatic hydrocarbon solvent solution of the methylaluminoxane with an aliphatic hydrocarbon solvent so as to cause said materials to precipitate from said solutions and then separating the precipitated solids from the methylaluminoxane solution. Optionally, following the removal of the solids from the solution, the aliphatic solvent can be removed, such as by distillation.

Also provided are clarified aluminoxane solutions prepared by the process and methylaluminoxanes obtained by the fractionation of a methylaluminoxane containing composition using a mixed aromatic/aliphatic hydrocarbon solvent system.

Methylaluminoxanes (MAO's) may exist in the form of linear or cyclic polymers. The methylaluminoxanes preferred for use in olefin polymerization catalysts usually contain about 5 to 40 or more of the repeating units:

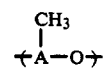

The methylaluminoxanes can contain minor portions of $C_2$ to $C_{10}$ alkyl groups and such materials are included within the term "methylaluminoxanes" as used herein. Methylaluminoxanes normally have lower solubility in organic solvents than higher alkylaluminoxanes and the methylaluminoxane solutions tend to be cloudy or gelatinous due to the separation of particles and agglomerates. This problem is frequently encountered with MAO which have been prepared by adding free water, either neat or contained in a solvent, to a solution of trimethylaluminum as described, for example, in Manyik et al. U.S. Pat. No. 3,300,458 referred to above. According to such processes, the water-alkylaluminum reaction is carried out in an inert solvent. The preferred solvents are aromatic hydrocarbons such as benzene, toluene, xylene, ethylbenzene, cumene, mesitylene and the like including mixtures thereof. The methylaluminoxane products contain varying amounts of from about 5 to 35 mole percent of the aluminum as unreacted trimethylaluminum.

The process of the invention treats an aromatic hydrocarbon solvent solution of MAO, which contains from about 0.5 to 30 weight percent aluminum values, with an aliphatic hydrocarbon solvent to cause the gel and gel forming materials to separate from the solution. The gel and gel forming materials, which are in the form of finely divided particles, are then easily removed by conventional means such as filtration or decantation of the solution.

An amount of aliphatic hydrocarbon solvent is selected to remove the gel and gel forming materials while minimizing the loss of the desirable aluminum values. Preferably, proportions of from about 0.5 to 10 parts by weight of aliphatic hydrocarbon solvent per part by weight of aromatic hydrocarbon solvent solution are employed.

Suitable aliphatic solvents include, but are not limited to, linear and cyclic aliphatic hydrocarbons having from about 5 to 7 carbon atoms, including mixtures thereof. Illustrative examples of such aliphatic solvents include pentane, isopentane, hexane, cyclohexane, heptane, Isopar C and the like. Preferably, an aliphatic solvent is selected whose boiling point is sufficiently lower than the aromatic solvent to permit the aliphatic solvent to be easily removed from the aromatic solvent solution by vacuu distillation after the gel and other solids are removed from the solution.

The fractionation treatment to remove gel and gel forming materials can be accomplished by adding the aliphatic hydrocarbon solvent to the alkylaluminoxane aromatic solvent solution and stirring vigorously for from about 1 to 15 hours at from ambient temperatures (15°–30° C.) up to the boiling point of the aliphatic hydrocarbon solvent and, preferably, from about 25° to 70° C. The treatment time is not particularly critical and longer or shorter times which are effective to transform the gels and particles and/or other gel forming materials to an easily filterable form can be used.

After the treatment, the solids are conveniently removed from the solution by filtration but they can also be removed by any conventional liquid-solid separation technique such as by centrifugation and decanting the liquid. Following the removal of the solids, the aliphatic solvent can be removed by vacuum distillation. Alternatively, the solution can remain as a mixed solvent solution or can be evaporated to dryness to recover a solid methylaluminoxane which can be readily redissolved in an aromatic solvent. The process of the invention not only provides clear, gel free solutions but the solutions are stable in that they remain gel free for extended periods of time. Besides removing the gel and gel forming materials, by controlling the process parameters, such as the solvent ratios, the methylaluminoxane can be further fractionated into different portions, depending upon the extent of their solubility in the mixed solvent system, for use in specific applications. For example, the methylaluminoxane can be fractionated to provide high (1801 to 3400), medium (1201 to 1800) and low (700 to 1200) number average molecular weight (freezing point depression) portions. Also, it has been found, as shown in the data reported in the tables, that, although the unreacted TMA would be expected to remain in solution, the process can act to reduce the TMA content of the aluminoxane product. This unexpectedly provides soluble methylaluminoxane products having a lower TMA content than can be achieved by stripping techniques. The mechanism is not understood, but analysis has shown that TMA is present in the precipitated materials. The process can provide fractionated methylaluminoxane products having low (1 to 12), medium 13 to 20) and high (21 to 35) mole percent) trimethylaluminum contents.

The invention is further illustrated by, but is not intended to be limited to, the following examples in which the crude methylaluminoxane was prepared by direct water hydrolysis of a trimethylaluminum solution in toluene.

General Procedures

All experiments were carried out under inert atmosphere conditions, using Schlenk glassware and a vacuum line, in conjunction with a $N_2$-dry box. Solvents were dried using standard methods. Filtration and vacuum distillation were done inside the $N_2$-dry box and distillates were collected in a trap at $-78°$ C. Number average molecular weights were determined by the freezing point depression method after recovering the fractionated MAO products by removing the solvents and then re-dissolving the solid MAO's in benzene. The samples are prepared in nominal concentrations of 0.04 to 0.05 g sample/g benzene. The sample is run in sets of four replicates with sixteen individual replicates within each of four sample replications. This is accomplished using a computer controlled apparatus. The precision of this method is not known for MAO samples due to the difficulty of obtaining a stable standard. With polystyrene standards of similar molecular weight, the precision is of the order of $+/-6\%$. It is estimated that for MAO samples the precision is in the order of $+/-10\%$.

EXAMPLE 1

A concentrated toluene/MAO solution (50 g, 300 mmol Al) was placed in a reaction vessel. Isopentane (150 g) was added. The mixture was vigorously stirred during a period of about 5 hours. The resulting solution was filtered to remove the precipitated solids and gave a clear toluene/isopentane solution of MAO.

The product was concentrated to dryness by vacuum distillation. Analysis of the solid MAO product is shown in Table 1.

EXAMPLE 2

Isopentane (200 g) was added to a toluene solution of MAO (50 g, 300 mmol Al) according to the procedure described in Example 1. Analysis of the solid product is given in Table 1.

EXAMPLE 3

Example 3 was carried out as described in Example 1 except that 300 g of isopentane was employed.

EXAMPLE 4

Concentrated toluene MAO solution (50 g, 300 mmol Al) was placed in a reaction tube. Hexane (150 g) was added and the mixture was magnetically stirred for abut 8 hours. The resulting solution was filtered to give a clear solution.

This solution was concentrated to dryness to give a colorless, free flowing solid. Analysis of the solid product is given in Table 1.

EXAMPLE 5

Example 5 was performed as described in Example 4 except that 200 g of hexane were added to the MAO solution (50 g).

EXAMPLE 6

Hexane (300 g) was added to MAO solution (50 g, 300 mmol Al) as described in Example 4. The resulting clear solution after filtration and evaporation gave a colorless, solid MAO product.

EXAMPLES 7, 8 and 9

These examples were carried out as described in Example 1 except that, to the MAO solution (50 g, 300 mmol Al) were added, respectively, 150 g, 200 g and 300 g of Isopar C.

The final solid products were characterized and the results are shown in Table 1.

EXAMPLE 10

Methylaluminoxane solution (50 g, 300 mmol Al) was placed in a reaction tube. Then, cyclohexane (150 g) was added. The resulting slurry was vigorously stirred at room temperature for about 12 hours. The mixture was filtered. The clear liquid product was evaporated to dryness under reduced pressure. A white colorless solid product was obtained. This is very easily dissolved in toluene to give a clear colorless solution. The solution remained clear after 2 months.

EXAMPLES 11 and 12

MAO (50 g, 300 mmol Al) was treated with cyclohexane, 200 g and 300 g, respectively. The reactions were carried out as described in Example 10. Analysis of the products is given in Table 1.

TABLE 1

Fractionation of MAO by Solvent Extraction

| Examples | Reaction Conditions | Soluble Al Value Recovered (Out of 300 mmol) MMol Al | % | TMA Content (Pyridine Titr) Mol % | Number Ave. Molecular Wt. |
|---|---|---|---|---|---|
| 1 | MAO/IP/150 | 120 | 40 | 7 | 1350 |
| 2 | MAO/IP/200 | 132 | 44 | 18 | 1094 |
| 3 | MAO/IP/300 | 174 | 58 | 10 | 1310 |
| 4 | MAO/Hex/150 | 159 | 53 | 1 | 1860 |
| 5 | MAO/Hex/200 | 156 | 52 | 15 | 901 |
| 6 | MAO/Hex/300 | 171 | 57 | 7 | 1290 |
| 7 | MAO/IC/150 | 126 | 42 | 29 | 1220 |
| 8 | MAO/IC/200 | 165 | 55 | 12 | 1210 |
| 9 | MAO/IC/300 | 170 | 57 | 23 | 1115 |
| 10 | MAO/Cyclohex/150 | 162 | 54 | 21 | 1310 |
| 11 | MAO/Cyclohex/100 | 198 | 66 | 32 | 2600 |
| 12 | MAO/Cyclohex/300 | 209 | 69 | 25 | 828 |

- IP = Isopentane; Hex = Hexane: IC = Isopar C and Cyclohex = Cyclohexane
- Starting material = 50 g solution (300 mmol Al)
- MAO/IP/150 = Isopentane (150 g) added to 50 g MAO solution The previous examples show an average soluble aluminum recovery of about 55% of the original value. However, if extra toluene is added to the initial 50 g of MAO before the extraction with alkane, a significant increase of extracted soluble aluminum value is observed. A similar increase in soluble aluminum value is also observed by applying heat to the toluene/alkene slurry of MAO.

Examples 13 to 16 illustrate the former effect while Examples 17 to 21 illustrate the latter effect. The average soluble aluminum recovery increased to about 75% of the original aluminum value.

EXAMPLE 13

MAO (50 g, 300 mmol Al) was placed in a reaction tube and then toluene (100 g) and cyclohexane (100 g) were added successively. The mixture was magnetically stirred during a period of about 12 hours. After filtration to remove the precipitated solids, a clear colorless solution was obtained. The product solution was concentrated to dryness at reduced pressure to give a colorless, free flowing solid. Analysis of the solid MAO product is given in Table 2.

EXAMPLE 14

Example 14 was carried out as described in Example 13 except using Isopar C. Analysis of the solid product is given in Table 2.

EXAMPLES 15 and 16

Examples 15 and 16 were done as described in Example 13, except that the extracting alkane solvents were hexanes and isopentane. After work-up to remove the solids, the products were only concentrated to 18.4 wt. percent Al and 8.8 wt. percent Al, respectively. These concentrated solutions remained clear and gel-free after about 2 months. Thus, the initial gelatinous toluene MAO solution had been clarified, by the mixed solvent system described above, to give gel-free toluene MAO solution, the volatile alkane solvent having been essentially removed by vacuum distillation.

TABLE 2

Effect of Additional Toluene* Solvent on Soluble Al Extraction

| Examples | Reaction Conditions | Soluble Al Value Recovered (Out of 300 mmol) MMol Al | % | TMA Content (Pyridine Titr) Mole % | Ave. Number Molecular Wt. |
|---|---|---|---|---|---|
| 13 | MAO/Tol/Cyclohex (100/100) | 232 | 77 | 15 | 1111 |
| 14 | MAO/Tol/IC (100/100) | 207 | 69 | 33 | 1990 |
| 15 | MAO/Tol/Hex (100/100) | 189 | 63 | 18 | L |
| 16 | MAO/Tol/IP (100/100) | 205 | 68 | 21 | L |

- Hex = Hexane; IC = Isopar C; IP = Isopentane
- Starting material = (50 g solution, 300 mmol Al)
- (50/150) = 50 g toluene and 150 g alkane
- *Al recovery without additional toluene was approx. 50%
- L = Left in concentrated liquid form

EXAMPLE 17

To a toluene slurry of MAO (50 g, 300 mmol Al) in a safety screw top reaction tube was added cyclohexane (150 g). The tube was heated in an oil bath at 70° C. for about 4 hours. The tube was brought back into a N₂-box where it was filtered. A colorless solution resulted. This solution was concentrated to dryness under reduced pressure. The final solid product is colorless and extremely air sensitive. 85% of the original aluminum value was recovered in the solid product. Analysis of the solid product product is given in Table 3.

EXAMPLES 18, 19 and 20

These Examples were carried out as described in Example 17, except that Isopar C, hexane and isopentane, respectively, were employed as the extracting alkane solvents. Analytical data for these products are shown in Table 3.

EXAMPLE 21

A MAO slurry in toluene (50 g, 300 mmol Al) was placed in a reaction tube. Additional tube (100 g) was added followed by isopentane (100 g). The mixture was heated at 70° C. (oil bath) for about 2 hours. After filtration, a colorless liquid was obtained. This liquid was concentrated at reduced pressure to 11.71 wt. percent Al solution containing 255 mmol of aluminum, which is 85% of the original aluminum value. This liquid product remained colorless and gel-free on standing for over 2 months. During such a period, an untreated MAO solution of this concentration would have started to form gels.

TABLE 3

Effect of Heating on Soluble Al Extraction

| Examples | Reaction Conditions | Soluble Al Value Recovered (Out of 300 mmol) MMol Al | % | TMA Content (Pyridine Titr) Mole | Ave. Number Molecular Wt. |
|---|---|---|---|---|---|
| 17 | MAO/Tol/Cycloh ex (50/150)/Heat | 255 | 85 | 17 | 2980 |
| 18 | MAO/Tol/IC (50/150)/Heat | 214 | 71 | 16 | 1940 |
| 19 | MAO/Tol/Hex (50/150)/Heat | 179 | 59 | 14 | 1725 |
| 20 | MAO/Tol/IP (50/150)/Heat | 161 | 54 | 21 | 1980 |
| 21 | MAO/Tol/IP | 256 | 85 | 20 | L |

TABLE 3-continued

Effect of Heating on Soluble Al Extraction

| Examples | Reaction Conditions (100/100)/Heat | Soluble Al Value Recovered (Out of 300 mmol) MMol Al % | TMA Content (Pyridine Titr) Mole | Ave. Number Molecular Wt. |
|---|---|---|---|---|

- Hex = Hexane; IC = Isopar C; IP = Isopentane
- Starting material = (50 g solution, 300 mmol Al)
- (50/150) = 50 g toluene and 150 g alkane
- L = Left in concentrated liquid form

What is claimed is:

1. A process for the removal of gel and gel forming materials from methylaluminoxane; said process comprising mixing an aromatic hydrocarbon solution of methylaluminoxane with an aliphatic hydrocarbon solvent so as to cause said materials to precipitate from said solution and then separating the precipitated solids from the methylaluminoxane solution.

2. The process according to claim 1 wherein said aromatic hydrocarbon solution of methylaluminoxane contains from about 0.5 to 30 weight percent aluminum values and the relative proportions of aliphatic hydrocarbon solvent to aromatic hydrocarbon solvent solution of methylalunminoxane are from about 0.5 to 10 parts by weight of aliphatic hydrocarbon solvent per part by weight of aromatic hydrocarbon solvent solution of methylaluminoxane.

3. The process according to claim 1 wherein the aliphatic hydrocarbon solvent has a lower boiling point than the aromatic hydrocarbon and said process included the step of removing the aliphatic hydrocarbon solvent from the solution.

4. The process according to claim 3 wherein the solids are separated by filtration and the aliphatic hydrocarbon solvent is removed from the solution by distillation.

5. The process according to claim 1 wherein the aromatic hydrocarbon solvent is toluene.

6. The process according to claim 1 wherein, after separation of the solids from the solution, the solvents are removed to recover a solid, aromatic hydrocarbon solvent soluble methylaluminoxane.

7. The process according to claim 1 wherein the methylaluminoxane contains essentially only methyl groups.

8. A methylaluminoxane solution prepared in accordance with the process of claim 1.

9. A methylaluminoxane solution prepared in accordance with the process of claim 2.

10. A methylaluminoxane solution prepared in accordance with the process of claim 3.

11. A solid, aromatic hydrocarbon solvent soluble methylaluminoxane prepared in accordance with the process of claim 6.

12. A process for fractionating a methylaluminoxane containing composition; said process comprising forming a mixture of said composition with a solvent system, said solvent system comprising a mixture of an aromatic hydrocarbon solvent and an aliphatic hydrocarbon solvent in relative proportions of aliphatic hydrocarbon solvent to aromatic hydrocarbon solvent of from about 0.5 to 10 parts by weight of aliphatic hydrocarbon solvent per part by weight of aromatic hydrocarbon solvent such that a less soluble methylaluminoxane component of said composition separates from said solvent system as a solid, and then removing said solid from said solvent system so as to obtain a solid methylaluminoxane fraction of said composition and a clear solution of the remaining methylaluminoxane in said solvent system, which solution contains from about 40 to 85% of the original aluminum value in said composition.

13. The process of claim 12 wherein said clear solution contains from 52 to 85% of the original aluminum value in said composition.

14. A methylaluminoxane product obtained by the fractionation of a methylaluminoxane containing composition using a mixed aromatic hydrocarbon/aliphatic hydrocarbon solvent system to separate insoluble material from said composition, wherein said methylaluminoxane product has a reduced trimethylaluminum content compared to said methylaluminoxane containing composition as a result of said fractionation.

15. A methylaluminoxane product according to claim 14 wherein said methylaluminoxane product contains from about 1 to 12 mole percent trimethylaluminum.

16. A methylaluminoxane product according to claim 14 wherein said methylaluminoxane product contain from about 13 to 20 mole percent trimethylaluminum.

17. A methylaluminoxane product according to claim 14 wherein said methylaluminoxane product contains from about 21 to 35 mole percent trimethylaluminum.

18. An aromatic hydrocarbon solvent soluble methylaluminoxane obtained by the fractionation of a methylaluminoxane composition using a mixed aromatic hydrocarbon/aliphatic hydrocarbon solvent system, said methylaluminoxane being free of gel and gel forming materials.

19. A methylaluminoxane product according to claim 18 wherein said methylaluminoxane product has a number average moledular weight of from about 700 to 1200.

20. A methylaluminoxane product according to claim 18 wherein said methylaluminoxane product has a number average molecular weight of from about 1201 to 1800.

21. A methylaluminoxane product according to claim 18 wherein said methylaluminoxane product has a number average molecular weight of from about 1801 to 3000.

* * * * *